United States Patent
Doemer et al.

(10) Patent No.: US 11,432,743 B2
(45) Date of Patent: Sep. 6, 2022

(54) RESPIRATION DEVICE WITH PRESETTING OF A PATIENTS INDIVIDUAL PRESSURE PROFILE

(71) Applicant: Loewenstein Medical Technology S.A., Luxembourg (LU)

(72) Inventors: Benno Doemer, Ettlingen (DE); Ruediger Alshut, Karlsruhe (DE); Matthias Schwaibold, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 984 days.

(21) Appl. No.: 15/854,027

(22) Filed: Dec. 26, 2017

(65) Prior Publication Data
US 2018/0177433 A1    Jun. 28, 2018

(30) Foreign Application Priority Data
Dec. 23, 2016    (DE) .......................... 102016015441.1

(51) Int. Cl.
*A61B 5/087*    (2006.01)
*A61M 16/00*    (2006.01)
(Continued)

(52) U.S. Cl.
CPC .............. *A61B 5/087* (2013.01); *A61B 5/082* (2013.01); *A61B 5/097* (2013.01); *A61M 16/024* (2017.08);
(Continued)

(58) Field of Classification Search
CPC . A61B 5/0002; A61B 5/02007; A61B 5/0205; A61B 5/02108; A61B 5/02116; A61B 5/0215; A61B 5/02152; A61B 5/02416; A61B 5/0295; A61B 5/08; A61B 5/0816; A61B 5/082; A61B 5/0836; A61B 5/087; A61B 5/0871; A61B 5/091; A61B 5/1135; A61B 5/14542; A61B 5/1455; A61B 5/4818; A61B 5/4833; A61B 5/4836; A61B 5/4839; A61B 5/6803; A61B 5/7235; A61B 5/7239; A61B 5/7246; A61B 5/7282; A61B 5/742; A61M 16/00;
(Continued)

(56) References Cited

U.S. PATENT DOCUMENTS

| 4,550,726 A * | 11/1985 | McEwen | ........... A61M 16/0051 128/202.22 |
| 7,305,987 B2 * | 12/2007 | Scholler | ............... A61B 5/0816 128/204.18 |

(Continued)

FOREIGN PATENT DOCUMENTS

| DE | 102007039004 A1 | 3/2008 |
| DE | 102009041247 A1 | 3/2011 |

(Continued)

*Primary Examiner* — Margaret M Luarca
(74) *Attorney, Agent, or Firm* — Abel Schillinger, LLP

(57) ABSTRACT

Disclosed is a device for respiration with at least one pressurized gas source for respiratory gas and a sensor unit for determination of respiratory gas pressure and/or flow rate and/or volume and a control unit. The control unit records an individual breathing pattern of a patient and from this forms an individual pressure profile for the patient which is provided by the pressurized gas source.

20 Claims, 4 Drawing Sheets

(51) Int. Cl.
*A61B 5/08* (2006.01)
*A61M 16/06* (2006.01)
*A61B 5/097* (2006.01)

(52) U.S. Cl.
CPC ...... *A61M 16/026* (2017.08); *A61M 16/0605* (2014.02); *A61M 16/0003* (2014.02); *A61M 2016/0036* (2013.01); *A61M 2205/3334* (2013.01); *A61M 2205/502* (2013.01); *A61M 2205/52* (2013.01)

(58) Field of Classification Search
CPC .......... A61M 16/0003; A61M 16/0009; A61M 16/0012; A61M 16/0045; A61M 16/0051; A61M 16/0066; A61M 16/0069; A61M 16/0078; A61M 16/0081; A61M 16/024; A61M 16/026; A61M 16/0627; A61M 16/0633; A61M 16/0677; A61M 16/0683; A61M 16/0833; A61M 16/085; A61M 16/0858; A61M 16/1015; A61M 16/1055; A61M 16/1065; A61M 16/107; A61M 16/109; A61M 16/12; A61M 16/16; A61M 16/161; A61M 16/20; A61M 16/22; A61M 2016/0015; A61M 2016/0021; A61M 2016/0027; A61M 2016/0036; A61M 2016/0039; A61M 2016/0042; A61M 2016/102; A61M 2016/1025; A61M 2016/103; A61M 2202/0208; A61M 2205/15; A61M 2205/16; A61M 2205/18; A61M 2205/3365; A61M 2205/3368; A61M 2205/3553; A61M 2205/3584; A61M 2205/3592; A61M 2205/36; A61M 2205/50; A61M 2205/505; A61M 2205/52; A61M 2230/005; A61M 2230/04; A61M 2230/08; A61M 2230/205; A61M 2230/40; A61M 2230/42; A61M 2230/432; A61M 2230/435; A61M 2230/50; A61M 2230/62; A61M 2230/63; A61M 39/228; A61M 2205/3334; A61M 16/003; G06F 19/00; G16H 40/63; G16H 50/20; Y10T 137/7761; Y10T 137/8326
See application file for complete search history.

(56) References Cited

U.S. PATENT DOCUMENTS

| | | | |
|---|---|---|---|
| 2001/0039950 A1 | 11/2001 | Scholler et al. | |
| 2002/0023644 A1* | 2/2002 | Berthon-Jones | A61M 16/06 128/204.22 |
| 2003/0121519 A1* | 7/2003 | Estes | A61M 16/0069 128/204.18 |
| 2003/0154979 A1* | 8/2003 | Berthon-Jones | A61M 16/0003 128/204.18 |
| 2003/0192544 A1 | 10/2003 | Berthon-Jones et al. | |
| 2005/0241639 A1* | 11/2005 | Zilberg | A61M 16/0006 128/204.21 |
| 2006/0027234 A1* | 2/2006 | Gradon | A61M 16/024 128/204.21 |
| 2007/0227538 A1* | 10/2007 | Scholler | A61M 16/0063 128/204.18 |
| 2008/0082018 A1* | 4/2008 | Sackner | A61B 5/113 600/538 |
| 2011/0226248 A1 | 9/2011 | Duff et al. | |
| 2011/0245704 A1 | 10/2011 | Monsieurs et al. | |
| 2011/0297156 A1* | 12/2011 | Shelly | A61M 16/0003 128/204.23 |
| 2013/0247914 A1* | 9/2013 | Truschel | A61M 16/161 128/204.23 |
| 2014/0182589 A1 | 7/2014 | Kane et al. | |

FOREIGN PATENT DOCUMENTS

| | | |
|---|---|---|
| EP | 1136094 A2 | 9/2001 |
| EP | 1518579 A1 | 3/2005 |
| EP | 1129742 A2 | 9/2011 |

* cited by examiner

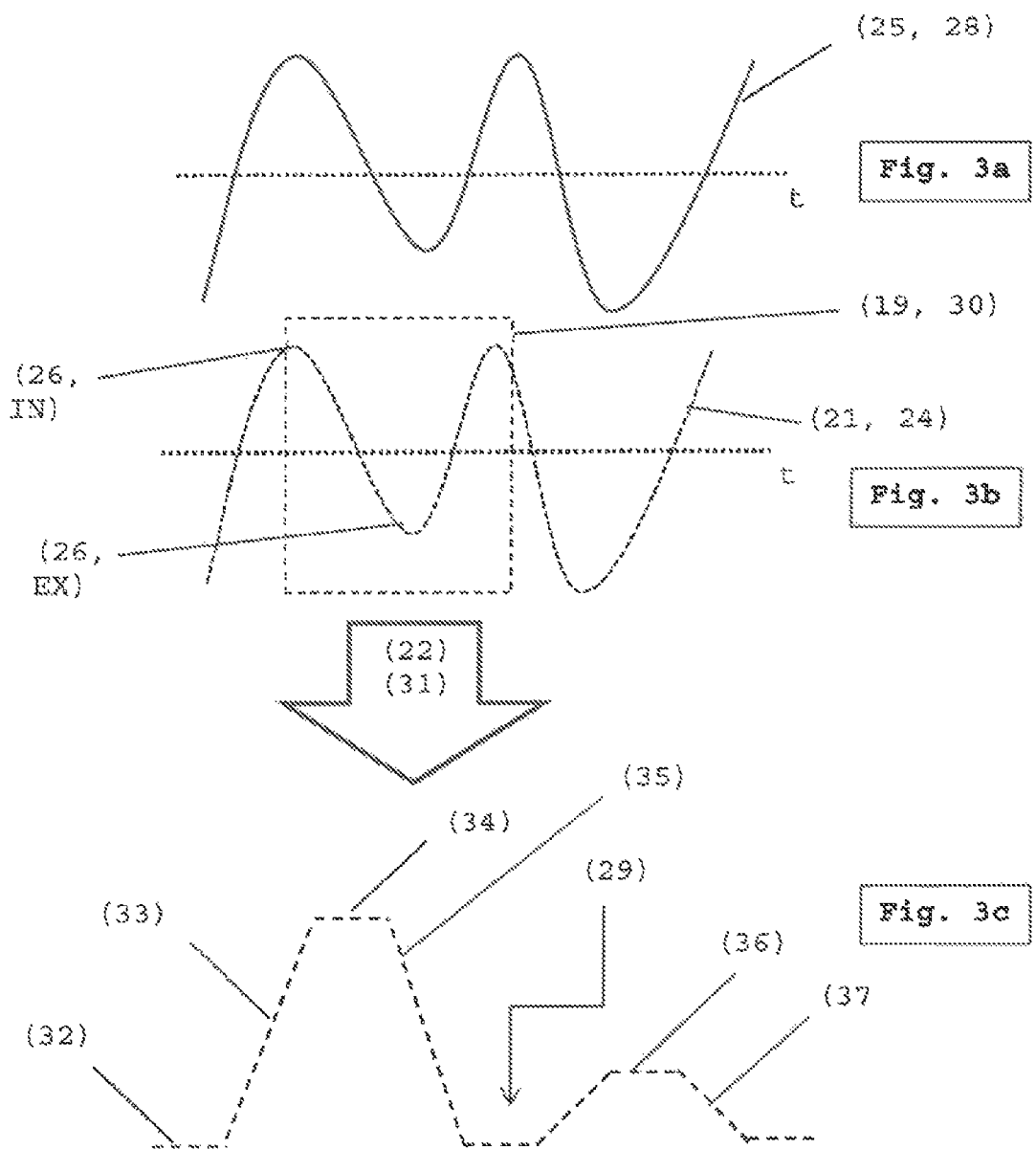

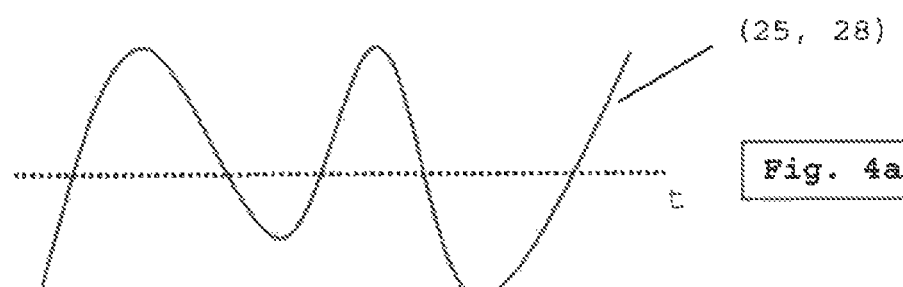
Fig. 4a
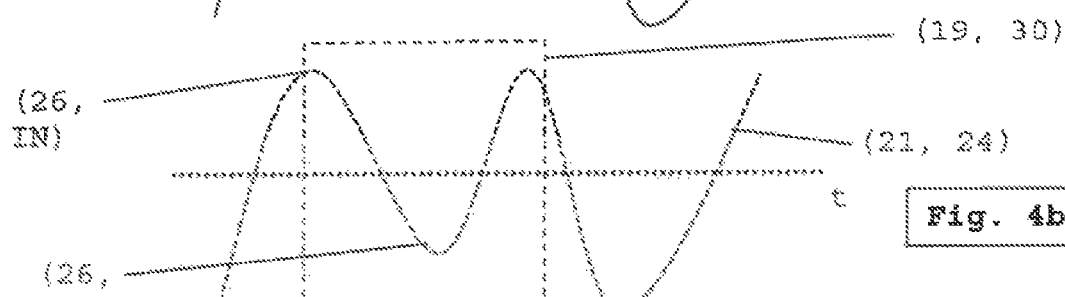
Fig. 4b
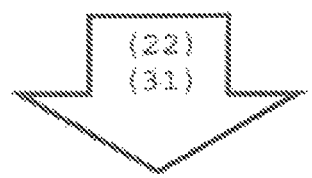
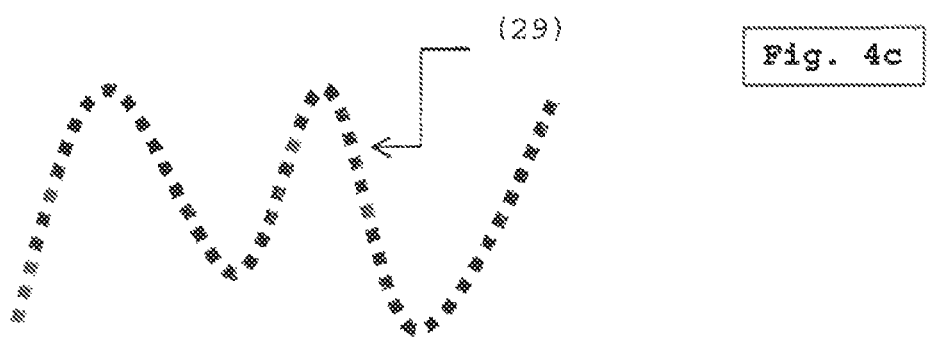
Fig. 4c

RESPIRATION DEVICE WITH PRESETTING OF A PATIENTS INDIVIDUAL PRESSURE PROFILE

CROSS-REFERENCE TO RELATED APPLICATIONS

The present application claims priority under 35 U.S.C. § 119 of German Patent Application No. 102016015441.1, filed Dec. 23, 2016, the entire disclosure of which is expressly incorporated by reference herein.

BACKGROUND OF THE INVENTION

1. Field of the Invention

The present invention relates to a respiratory device with a presetting of a patient's individual pressure profile.

2. Discussion of Background Information

Thus far in the process of respiration there are typically one (CPAP, APAP), two (Bilevel, ASV) or three (TRILevel) pressure levels, between which there is switching back and forth using certain breathing characteristics at switch points. The switching here can be in stages, or it can occur by linear or nonlinear ramps.

These forms of respiration are quite rigid and can only be used with few degrees of freedom for the individual breathing pattern of the patient and the therapy of his individual respiratory disease.

In view of the foregoing, it would be advantageous to make possible an individual adaptation to the patient's needs.

SUMMARY OF THE INVENTION

The present invention provides a device for respiration. The device comprises at least one pressurized gas source for respiratory gas, a sensor unit for determining respiratory gas pressure and/or flow rate and/or volume, a control unit, and a memory. The control unit comprises
  a curve analyzer, which determines and buffers a curve of at least one signal,
  a transform function, which converts by at least one mathematical mapping the curve of at least one signal into a pressure profile,
  a pressure profile applicator, which actuates the pressurized gas source as a function of the pressure profile.

In one aspect of the device, the control unit may convert the curve of respiratory gas flow rate and/or respiratory gas volume as current breathing pattern of a patient into the pressure profile and may actuate the pressurized gas source as a function of the pressure profile.

In another aspect, the transform function or the at least one mathematical mapping may additionally consider the presettings of a user.

In yet another aspect, the transform function may consider a memorized typical breathing pattern, which is formed as a function of at least two curves of the at least one signal, and a current breathing pattern of a patient, from the curve of the at least one signal.

In a still further aspect, the sensor unit may record the respiratory gas pressure and/or the flow rate and/or the volume with a resolution of at least 40 Hz, or a resolution greater than 40 Hz or greater than 60 Hz.

In another aspect, the control unit may buffer the curve of the at least one signal with reduced resolution of less than 40 Hz, or less than 30 Hz.

In another aspect, the cutout unit may be designed and set up to send defined time periods or time periods recognized from the curve of the at least on signal from the memory to a breathing pattern analyzer and/or a contour analyzer.

In another aspect, the control unit may further comprise a contour analyzer which recognizes, as breathing states or respiration states, an inspiration and/or an expiration and/or a patient trigger and/or a volume and/or an I to E ratio and/or artifacts and/or mouth expiration and/or COPD breathing and/or Cheyne-Stokes breathing. For example, the contour analyzer may recognize certain breathing states or respiration states by pattern comparison.

In another aspect of the device, the control unit may further comprise a breathing pattern analyzer, which analyzer or the transform function may use a current curve of the at least one signal and a memorized individual breathing pattern.

In another aspect, the transform function, by at least one mathematical mapping, may convert an individual breathing pattern into the pressure profile, and in doing so may also consider presettings of a user which are entered into the memory by an operating element or an operating and information system or an interface, wherein the pressure profile considers the individual breathing pattern and presettings of a user.

In another aspect, the pressure profile applicator may actuate the pressurized gas source as a function of the pressure profile, for example, in such a way that an optimized synchronization with a patient's own breathing occurs and/or the most comfortable possible respiration is preset and/or the breathing effort of the patient is as little as possible and/or the formation of an intrinsic PEEP is prevented and/or a certain minute ventilation is achieved and/or an anticyclic servoventilation occurs for treatment of certain pathological breathing patterns and/or obstructions of the airways are prevented and/or a certain tidal volume is achieved.

In another aspect of the device, the pressure profile may comprise a sequence of pressure levels and/or pressure waveforms and/or pressure plateaus and/or pressure ramps, substantially reflecting, at least in segments, corresponding segments. For example, the corresponding segments may include a frequency and/or an I/E ratio and/or a minute volume and/or inspirations and expirations, of a patient's breathing from the curve and/or a breathing pattern.

The present invention also provides a device for respiration, which device comprises at least one pressurized gas source for respiratory gas, a sensor unit for determining respiratory gas pressure and/or flow rate and/or volume, a control unit, and a memory. The control unit comprises
  a curve analyzer, which senses, analyzes and buffers the curve of at least one signal which stands in connection with or is the respiratory gas pressure, flow rate or volume,
  a cutout unit, which selects defined time periods, or time periods recognized from the curve, of the curve of the at least one signal and sends them to a breathing pattern analyzer and/or a contour analyzer,
  a contour analyzer, which recognizes from the curve of the at least one signal of a current time period the presence or absence of certain breathing states or respiration states, a breathing pattern analyzer, which ascertains the individual breathing pattern of a patient from at least two curves of the at least one signal, a transform function, which converts by at least one mathematical mapping the individual breathing pattern into a pressure profile, a pressure profile applicator, which actuates the pressurized gas source as a function of the pressure profile.

The present invention also provides a device for respiration, which device comprises at least one pressurized gas source for respiratory gas, a sensor unit for determining respiratory gas pressure and/or flow rate and/or volume, a control unit, and a memory. The control unit comprises a curve analyzer, which senses, analyzes and buffers a curve of at least one signal which stands in connection with the pressure, flow rate or volume, a cutout unit, which selects defined time periods, or time periods recognized from the curve, of the curve of at least one signal from a buffer memory and sends them to a breathing pattern analyzer and a contour analyzer, a contour analyzer, which recognizes from the curve of a current time period that was sent to it by the cutout unit the presence or absence of certain acute breathing states or respiration states, a breathing pattern analyzer, which ascertains the typical individual breathing pattern of a patient from at least two curves that were sent to it by the cutout unit, a transform function, which converts by at least one mathematical mapping the individual breathing pattern into a pressure profile which is valid for a current or following breath, a pressure profile applicator, which uses the results of the curve analyzer to optimize a specified pressure profile to the curve of a breath and sends a nominal pressure to the at least one pressurized gas source.

As set forth above, the present invention provides a device for respiration with at least one pressurized gas source for respiratory gas and a sensor unit for determination of respiratory gas pressure and/or flow rate and/or volume and a control unit, as well as a memory, wherein the control unit comprises a curve analyzer, which determines and buffers the curve of at least one signal, a transform function, which converts by at least one mathematical mapping the curve into a pressure profile, a pressure profile applicator, which actuates the pressurized gas source in consideration (as a function) of the pressure profile.

The device may also be characterized in that the control unit converts the curve of respiratory gas flow rate and/or respiratory gas volume as current breathing pattern of the patient into a pressure profile and actuates the pressurized gas source in consideration (as a function) of the pressure profile.

The device may also be characterized in that the transform function or the mathematical mapping additionally considers presettings of a user.

The device may also be characterized in that the transform function considers a memorized typical breathing pattern, which is formed in consideration of at least two of the curves, and a current breathing pattern of the patient, from the curve.

The device may also be characterized in that the sensor unit records respiratory gas pressure and/or flow rate and/or volume with a resolution of at least about 40 Hz or a resolution greater than about 40 Hz or greater than about 60 Hz.

The device may also be characterized in that the control unit buffers the curve of at least one signal with reduced resolution of less than about 40 Hz or less than about 30 Hz.

The device may also be characterized in that the cutout unit is designed and set up to send defined time periods or time periods recognized from the curve from the memory to the breathing pattern analyzer and/or the contour analyzer.

The device may also be characterized in that the contour analyzer recognizes, as breathing states or respiration states, an inspiration and/or an expiration and/or a patient trigger and/or the volume and/or the I to E ratio and/or artifacts and/or mouth expiration and/or COPD breathing and/or Cheyne-Stokes breathing.

The device may also be characterized in that the contour analyzer recognizes certain breathing states or respiration states by pattern comparison.

The device may alternatively also be characterized in that the breathing pattern analyzer or the transform function uses a current signal curve and a memorized individual breathing pattern.

The device may additionally also be characterized in that the transform function, by at least one mathematical mapping, converts the individual breathing pattern into a pressure profile, and in also doing so presettings of a user which are entered into memory by the operating element or the operating and information system or the interface, wherein the pressure profile considers the individual breathing pattern and the presettings of a user.

The device may also be characterized in that the pressure profile applicator actuates the pressurized gas source, in consideration (as a function) of the pressure profile, for example in such a way that an optimized synchronization with the patient's own breathing occurs and/or the most comfortable possible respiration is preset and/or the breathing effort of the patient is as little as possible and/or the formation of an intrinsic PEEP is prevented and/or a certain minute ventilation is achieved and/or an anticyclic servoventilation occurs for treatment of certain pathological breathing patterns and/or obstructions of the airways are prevented and/or a certain tidal volume is achieved.

The device may additionally or alternatively be also characterized in that the pressure profile comprises a sequence of pressure levels and/or pressure waveforms and/or pressure plateaus and/or pressure ramps, substantially reflecting, at least in segments, corresponding segments, such as the frequency and/or the I/E ratio and/or the minute volume and/or inspirations and expirations, of the patient's breathing from the curve and/or the breathing pattern.

The present invention also provides a device for respiration with at least one pressurized gas source for respiratory gas and a sensor unit for determination of respiratory gas pressure and/or flow rate and/or volume and a control unit, as well as a memory, wherein the control unit comprises a curve analyzer, which senses, analyzes and buffers the curve of at least one signal which stands in connection with or is the respiratory gas pressure, flow rate or volume, a cutout unit, which selects defined time periods, or time periods recognized from the curve, of the curve of at least one signal and sends them to the breathing pattern analyzer and/or the contour analyzer, a contour analyzer, which recognizes from the curve of the current time period the presence or absence of certain breathing states or respiration states, a breathing pattern analyzer, which ascertains the individual breathing pattern of a patient from at least two curves, a transform function, which converts by at least one mathematical mapping the individual breathing pattern into a pressure profile, a pressure profile applicator, which actuates the pressurized gas source in consideration (as a function) of the pressure profile.

The present invention also provides a device for respiration with at least one pressurized gas source for respiratory gas and a sensor unit for determination of respiratory gas pressure and/or flow rate and/or volume and a control unit, as well as a memory, wherein the control unit comprises a curve analyzer, which senses, analyzes and buffers the curve of at least one signal which stands in connection (is associated) with pressure, flow rate or volume, a cutout unit, which selects defined time periods, or time periods recognized from the curve, of the curve of at least one signal from the buffer memory and sends them to the breathing pattern analyzer and/or the contour analyzer, a contour analyzer, which recognizes from the curve of the of time period that was sent to it by the cutout unit the presence or absence of certain acute breathing states or respiration states, a breathing pattern analyzer, which ascertains the typical individual breathing pattern of a patient from at least two curves that were sent to it by the cutout unit, a transform function, which converts by at least one mathematical mapping the individual breathing pattern into a pressure profile which is valid for the current or following breath, a pressure profile applicator, which uses the results of the curve analyzer to optimize the specified pressure profile to the curve of the breath and to send the nominal pressure to the pressure source.

The present invention also provides a device for respiration with at least one pressurized gas source for respiratory gas and a sensor unit for determination of respiratory gas pressure and/or flow rate and/or volume and a control unit, as well as a memory, wherein the control unit comprises a) a curve analyzer, which senses, analyzes and buffers continuously (at least with about 1 Hz, preferably >about 20 Hz) the curve of at least one signal which stands in connection with pressure, flow rate or volume, b) a cutout unit, which selects defined time periods, or time periods recognized from the curve, of the curve of at least one signal from the buffer memory and sends them to the breathing pattern analyzer and the contour analyzer, c) a contour analyzer, which recognizes from the curve of the current time period that was sent to it by the cutout unit the presence or absence of certain acute breathing states or respiration states, d) a breathing pattern analyzer, which ascertains the typical individual breathing pattern of a patient from at least two curves that were sent to it by the cutout unit, e) a transform function, which converts by at least one given mathematical mapping the individual breathing pattern into a pressure profile which is valid for the current or following breath, f) a pressure profile applicator, which uses the results of the curve analyzer to optimize the specified pressure profile to the momentary curve of the breath and to send continuously from this (at least about 1 Hz, preferably >about 20 Hz) the momentary nominal pressure to the pressure source.

The present invention also provides a device for respiration with at least one pressurized gas source for respiratory gas and a sensor unit for determination of respiratory gas pressure and/or flow rate/and/or volume and a control unit. The control unit records an individual breathing pattern of a patient and from this forms an individual pressure profile for the patient which is provided by the pressurized gas source.

According to the invention, it is possible to measure the breathing of the patient with a high sample rate almost continuously (at least about 40 Hz, preferably >about 60 Hz) and then apply an ongoing adapted pressure profile, consisting of a number of predetermined pressure levels. IPAP and EPAP are applicable here as concepts at best still for minimum and maximum of the pressure profile. Neither is a conventional trigger necessary; the synchronism of pressure profile and breathing profile can be optimized in an ongoing and iterative manner. Thus, the machine learns in ongoing manner to predict the start of the next breath.

The corresponding device encompasses, besides the usual parts (pressure source, at least one hose, patient interface, pressure control, power supply, interfaces for the cloud etc., sensors for signals which stand in connection with pressure, flow rate or volume, etc.), the following characteristic points of the pressure control, for example:

Optionally, alternatively or additionally one or more of the following design possibilities may be implemented.

1) Curve analyzer, which senses, analyzes and buffers continuously (at least with 1 Hz, preferably >about 20 Hz, especially preferably >about 50 Hz) the curve of at least one signal which stands in connection with pressure, flow rate or volume.

2) Cutout unit, which sends defined time periods, or time periods recognized from the curve, of the curve of at least one signal from the buffer memory to the breathing pattern analyzer and/or the contour analyzer.

3) Contour analyzer, which recognizes from the curve of the current time period that was sent to it actively or passively by the cutout unit the presence or absence of certain acute breathing states or respiration states.

4) Breathing pattern analyzer, which ascertains the typical individual breathing pattern of a patient from at least 2 curves that were sent to it actively or passively by the cutout unit.

5) Transform function, which converts by at least one given mathematical mapping the individual breathing pattern into a pressure profile which is valid for the current or following breath.

6) Pressure profile applicator, which uses the results of the curve analyzer to optimize the specified pressure profile to the momentary curve of the breath and to send continuously from this (at least about 1 Hz, preferably >about 20 Hz, especially preferably >about 50 Hz) the momentary nominal pressure to the pressure source.

Curve Analyzer:

A sample, not exhaustive list of possible signal types which the curve analyzer analyzes are: machine flow rate, patient flow rate, patient flow rate with flushing flow rate, pressure at the machine outlet, pressure in the mask, pressure in the airways, current tidal volume, current alveolar tidal volume as well as estimated values for one of these signals or signals related to them.

A sample, not exhaustive list of possible analyses which the curve analyzer performs are: recognition of the breath phase, recognition of the current moment within the curve of a breath, recognition of rising or falling volume with respect to the individual breathing pattern or the immediately prior breaths, synchronism of pressure curve and patient breathing.

Cutout Unit

Beginning and end of the time periods are defined for example by: fixed durations, for example fixed second count or 1/breath rate, or by characteristic points such as passing through zero of at least one of the analyzed signals after subtracting an offset, inspiration beginning, expiration beginning, inspiratory peak flow rate, expiratory peak flow rate, attainment of a given pressure value, maximum or minimum gradient of a signal or passing through zero of the gradient, maximum or minimum curvature of the signal or its passing through zero, beginning or end of a complete breath, attainment of a particular volume, etc.

Contour Analyzer:

A sample, not exhaustive list of possible recognized breathing states or respiration states:

flattening in the inspiration due to obstruction of the upper airways flattening or instabilities in the expiration by obstruction of the lower airways, secretion, COPD mask or mouth leakage skipped breaths artifact conditions such as movement, speaking, coughing, swallowing, etc.

synchronism or current time offset of pressure curve and breathing curve current breathing effort current active resistance to the respiration current tidal volume, alveolar tidal volume, minute volume, alveolar minute volume (alveolar volumes by allowing for a ventilator dead space which is manually given or automatically estimated by the machine)

current volume demand resistance and/or compliance of the airways and lungs or values related to this.

From at least 2 individual breathing pattern curves, the individual breathing pattern of the patient is determined, for example, by at least one of the following steps normalization of current breathing patterns in time and flow rate or volume averaging of individual breathing patterns weighted averaging of individual breathing patterns, wherein the weighting depends for example on duration, peak flow rate, mean flow rate, volume or the conditions recognized by the contour analyzer (for example low weight upon occurrence of flattening or artifacts, etc.)

least-squares fitting or related fitting of a current estimate of the individual breathing pattern to the actual breathing pattern of the current unit of time moving average of the curve of several units of time elimination of a time offset of breathing patterns within at least 2 units of time smoothing of the breathing pattern, for example to eliminate distortions, for example due to flattening.

The mathematical mapping may involve, for example:

presettings based on the disease syndrome, for example an optimized pressure profile for restrictive or obstructive lungs; the disease syndrome may here either be specified by the user, or automatically identified by the respirator machine presettings for the therapy goal, for example minimization of breathing effort, stabilization of the CO2 value, optimization of patient comfort, avoidance of an intrinsic PEEP during the respiration, maintaining of a target value for tidal volume, alveolar tidal volume, minute volume, alveolar minute volume, treatment of obstructions of the upper airways, stabilization of the SpO2 value, ensuring a minimum or maximum pressure stroke, avoidance of dangerous situations, etc.; the presettings may be selected here by the user or stored permanently in the machine universal functions stored permanently in the machine for converting a breathing pattern into a suitable pressure profile steps to optimize the synchronism of pressure profile and breathing effort of the patient, for example by extending or compressing the pressure profile steps to speed up or slow down the breathing optionally, the transform function may resort here to other signals from the outside, especially: SpO2, CO2, pulse wave, effort, heart rate, data entry by patient or medical staff, EMG of the respiratory muscles, breathing noises, breathing strain or to the results of the contour analyzer, for example in order to respond to obstructions of the upper airways by increasing/lowering the pressure profile, to control one of the mentioned volumes or to improve the synchronism of respiration and breathing effort of the patient by accelerating/slowing down the pressure profile or to lessen intrinsic PEEP.

The pressure profile applicator optimizes the pressure profile for the current breath curve using the results of the curve analyzer:

in particular to deal with deviations of the current breathing curve from the individual breathing pattern for example, the optimization may be done such that the deviation is supported or counteracted deviations are determined in particular in regard to magnitude of flow rate/volume, alveolar flow rate/volume or acceleration/slowing down of the breathing the optimization is done, for example, by a mathematical mapping, especially using the results of the contour analyzer or by scaling of the pressure profile ascertained by the mathematical mapping in terms of magnitude or duration/velocity.

The control unit (16) is designed and set up so that it has as functional units a curve analyzer (18) and/or a cutout unit (19) and/or a breathing pattern analyzer (21) and/or a contour analyzer (20) and/or a transform function (22) and/or a pressure profile applicator (23). The control unit (16) may have all of the aforementioned functional units or only some of them. In particular, the control unit may also itself execute all of the functions according to the invention, without the self-standing functional units being necessary.

BRIEF DESCRIPTION OF THE DRAWINGS

Further benefits and features of the present invention will emerge from the description of the exemplary embodiments, which will be explained with reference to the accompanying drawings.

In the drawings,

FIG. 3a illustrates how a complete or partial breath is recorded for the determination of respiratory gas pressure and/or flow rate and/or volume, as a signal, FIG. 3b illustrates the selection of defined time periods of the curve shown in FIG. 3a, FIG. 3c illustrates the conversion of the curve shown in FIG. 3b by at least one mathematical mapping into a pressure profile for a patient, FIG. 4a illustrates how a complete or partial breath is recorded for the determination of respiratory gas pressure and/or flow rate and/or volume, as a signal, FIG. 4b illustrates the selection of defined time periods of the curve shown in FIG. 4a, and FIG. 4c illustrates the conversion of the curve shown in FIG. 4b by a transform function into a pressure profile for a patient by at least one mathematical mapping.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
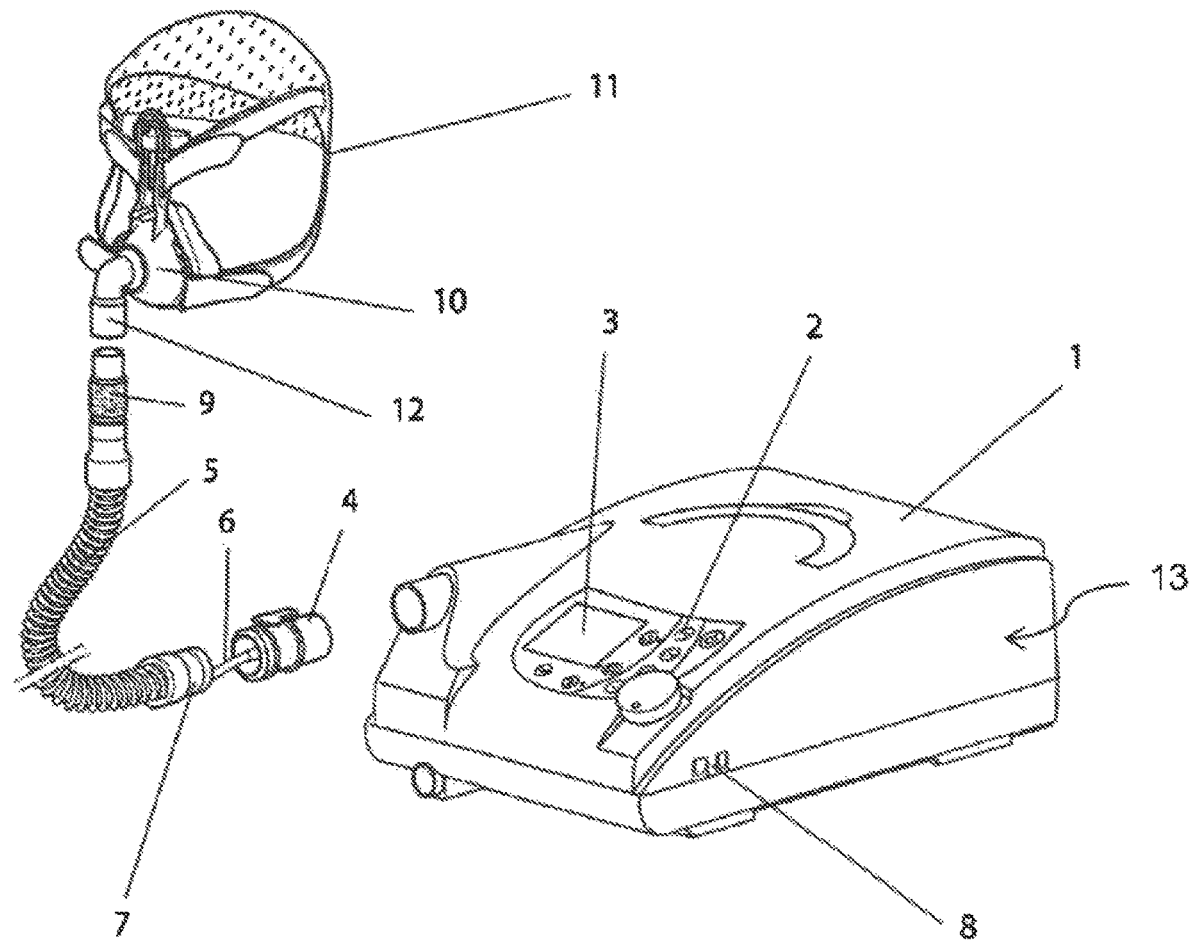
FIG. 1 shows the fundamental layout of a device for respiration.

FIG. 1 shows the fundamental layout of a device for respiration. In the area of a machine housing (1) of the respirator machine (13), having a respiratory gas source in the interior of the machine, there are an operating element (2) and an operating and information system consisting of a display (3), which may have a data entry unit, such as a touch-sensitive unit, with at least one control pad. By a coupling (4), a connection hose (5) is attached. Along the connection hose (5) there may run an additional pressure measuring hose (6), which can be connected by a pressure inlet nozzle (7) to the machine housing (1). To enable a data transmission, the machine housing (1) has at least one interface (8). A humidifier can furthermore be adapted. In the area of an extension of the connection hose (5) facing away from the machine housing (1) there is arranged an exhalation element (9). An exhalation valve may also be used.

FIG. 1 furthermore shows a patient interface designed as a respirator mask (10), which is realized as a nasal mask. An attachment in the area of a head of a patient can be done by a head hood (11). In the area of its extension facing toward the connection hose (5), the patient interface (10) has a connection element (12).

Through the interface (8), data may be entered and/or output, such as dead volume. The interfaces can be realized as wired, infrared interface, Bluetooth interface or USB. A card slot is preferably also provided. The interface (8) may also be designed as a LAN interface or as some other interface for connection to the Internet. In the area of a machine housing, an oxygen connection valve can be adapted to the respiration device. It is conceivable to further enrich the respiratory gas with oxygen, in order to improve the patient care. Instead of one interface (8), a plurality of interfaces may also be provided.

Through the interface (8)—designed for example as a card slot or USB—it is also possible to load data not related to therapy into the respirator machine according to the invention or export data from it. For example, by this one has in mind representing photos or videos by means of storage media via the interface (8) in the area of the display. The user must—if external storage media are recognized by the machine—confirm a query in the operator pad, whereupon the data is optionally stored in the area of the respirator machine or exported.

The entry and/or output of telemedical data can be done through the interface (8). For this, mobile radio or near field radio data is received/sent for example across the interface, or WLAN or Bluetooth or network data.

The respirator machine (13) according to the invention is designed so that it can be connected to a patient by a hose and a patient interface in order to make ready a respiration procedure. It comprises a source of respiratory gas, which is designed for example as an electric motor with a blower wheel, and a device for determination of pressure and/or flow rate and/or volume of the respiratory gas, as well as a control unit, which is designed so that it determines a respiratory gas pressure for each breathing cycle on the basis of a predetermined value for the patient and/or on the basis of measurement signals for the parameters of pressure and/or flow rate and/or volume and regulates the source of the respiratory gas so that the respiratory gas pressure is generated.

The control unit is moreover designed so that it determines the current pressure and/or flow rate and/or the volume of respiratory gas and represents the current value via the operating and information system connected to the control unit. The control unit is furthermore designed so that it determines trend changes in its computations over time, related to one or more parameters, wherein the trend changes can be shown on the display.

Furthermore, the control unit compares such parameter values, as have been preset by a user, such as upper and lower pressure limits or a maximum tolerable number of apneas per unit of time, or a maximum tolerable leakage, to the current values and generates user information on deviations from the presettings. The user information is preferably visualized graphically via the operating and information system.

Thus, apneas and hypopneas are recognized from the measured breathing flow rate by a decrease in the breathing (time) volume for a time period of at least 10 s. In addition, snoring is recognized by pressure and flow rate fluctuations, as well as a flattening by the inspiratory flow rate contour. From this, indices are calculated for every sufficiently long nighttime therapy, namely: AHI (=number of apneas+hypopneas per artifact-free therapy period), RDI (=number of all respiratory events per artifact-free therapy period), number of breaths with flattening, number of breaths with snoring. Preferably, data is also determined to allow conclusions to be drawn about the usage behavior or the duration of use of the machine by the patient. This data is determined and saved daily or weekly or monthly. If required, the usage data is retrieved and sent, possibly together with a machine identifier, via an Internet connection or mobile radio connection.

Figure 2:
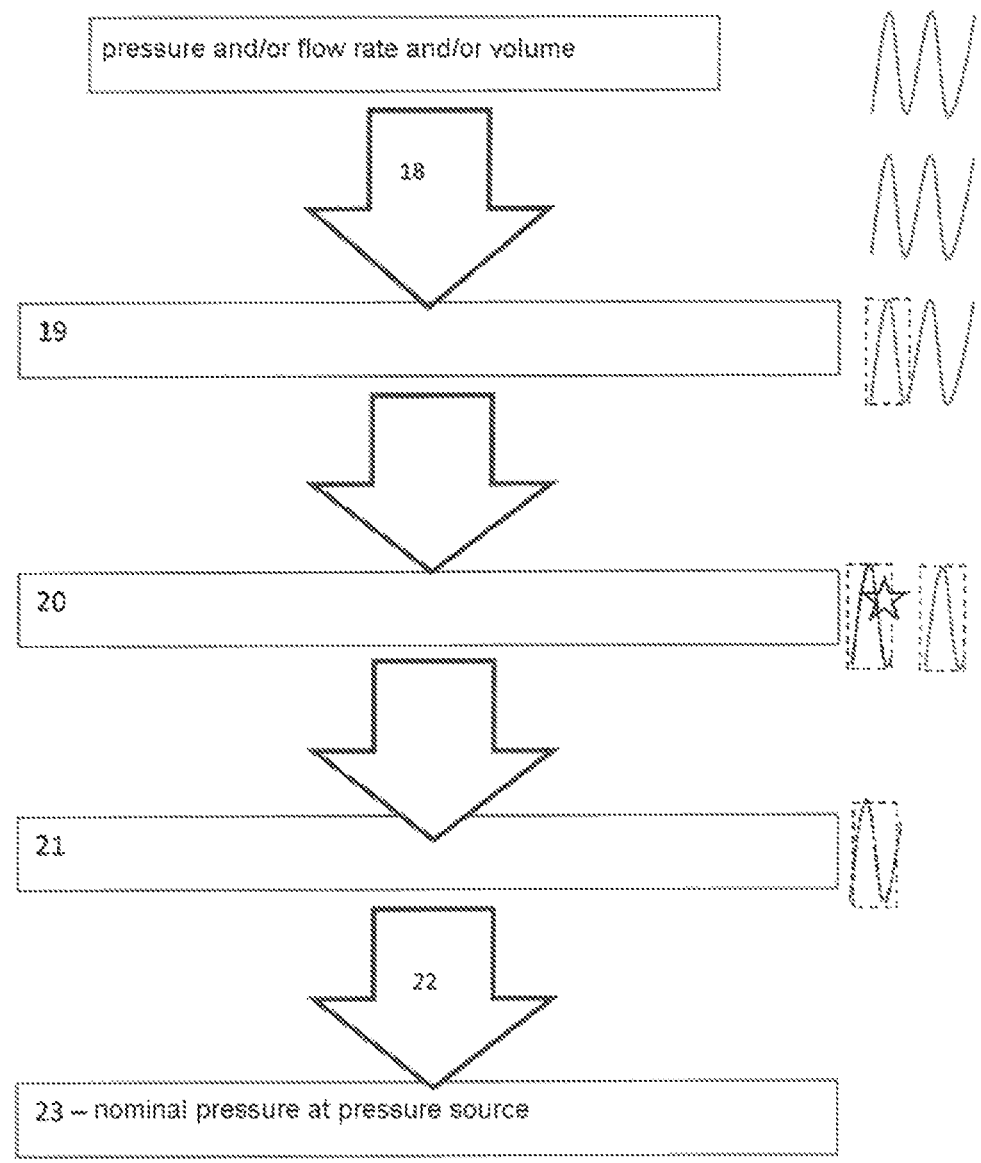
FIG. 2 is a flow diagram which shows how the device for respiration of the type shown in FIG. 1 determines from pressure and/or flow rate and/or volume values a nominal pressure for a pressurized gas source.

FIG. 2 shows how the device for respiration (13) with at least one pressurized gas source for the respiratory gas and a sensor unit for determination of respiratory gas pressure and/or flow rate and/or volume and a control unit, as well as a memory, determines from the pressure and/or flow rate and/or volume values a nominal pressure for the pressurized gas source. The control unit comprises a curve analyzer (18), which senses, analyzes and buffers in memory continuously (at least with 1 Hz, preferably >20 Hz) the curve of at least one signal which stands in connection with the pressure and/or flow rate and/or volume. The control unit furthermore comprises a cutout unit (19), which selects defined time periods, or time periods recognized from the curve of at least one signal which stands in connection with the pressure and/or flow rate and/or volume, of the curve of at least one signal from the buffer memory and sends them to the breathing pattern analyzer and the contour analyzer.

The control unit furthermore comprises a contour analyzer (20), which recognizes from the curve of the current time period that was sent to it by the cutout unit (19) the presence or absence of certain acute breathing states or respiration states.

The control unit furthermore comprises a breathing pattern analyzer (21), which ascertains the typical individual breathing pattern of a patient from at least two curves that were sent to it by the cutout unit.

The control unit furthermore comprises a transform function (22), which converts by at least one given mathematical mapping (31) the individual breathing pattern into a pressure profile (29) which is valid for the current or following breath.

The control unit furthermore comprises a pressure profile applicator (23), which uses the results of the curve analyzer to optimize the specified pressure profile to the momentary curve of the breath and to send from this (at least about 1 Hz, preferably >about 20 Hz) the nominal pressure to the pressure source.

The curve analyzer (18) recognizes, for example, as signal types: machine flow rate, patient flow rate, patient flow rate with flushing flow rate, pressure at the machine outlet, pressure in the mask, pressure in the airways, current tidal volume, current alveolar tidal volume as well as estimated values for one of these signals or signals related to them. As possible analyses, the curve analyzer (18) performs: recognition of the breath phase, recognition of the current moment within the curve of a breath, recognition of rising or falling volume with respect to the individual breathing pattern or the immediately prior breaths, synchronism of pressure curve and patient breathing.

The cutout unit (19) defines beginning and end of the time periods for example by: fixed durations, for example fixed second count or 1/breath rate, or by characteristic points such as passing through zero of at least one of the analyzed signals after subtracting an offset, inspiration beginning, expiration beginning, inspiratory peak flow rate, expiratory peak flow rate, attainment of a given pressure value, maximum or minimum gradient of a signal or passing through zero of the gradient, maximum or minimum curvature of the signal or its passing through zero, beginning or end of a complete breath, attainment of a particular volume.

The contour analyzer (20) recognizes possible breathing states or respiration states such as flattening in the inspiration due to obstruction of the upper airways, flattening or instabilities in the expiration by obstruction of the lower airways, secretion, COPD, mask or mouth leakage, skipped breaths, artifact conditions such as movement, speaking, coughing, swallowing, etc., synchronism or current time offset of pressure curve and breathing curve, current breathing effort, current active resistance to the respiration, current tidal volume, alveolar tidal volume, minute volume, alveolar minute volume (alveolar volumes by allowing for a ventilator dead space which is manually given or automatically estimated by the machine), current volume demand, resistance and/or compliance of the airways and lungs or values related to this.

From at least 2 individual breathing pattern curves, the individual breathing pattern of the patient is determined by the breathing pattern analyzer (21), by at least one of the following steps: normalization of current breathing patterns in time and flow rate or volume, averaging of individual breathing patterns, weighted averaging of individual breathing patterns, the weighting depend for example on duration, peak flow rate, mean flow rate, volume or the conditions recognized by the contour analyzer (for example low weight upon occurrence of flattening or artifacts, etc.), least-squares fitting or related fitting of a current estimate of the individual breathing pattern to the actual breathing pattern of the current unit of time, moving average of the curve of several units of time, elimination of a time offset of breathing patterns within at least 2 units of time, smoothing of the breathing pattern, for example to eliminate distortions, for example due to flattening.

The mathematical mapping (31) of the transform function (22) may involve:
  presettings based on the disease syndrome, for example an optimized pressure profile (29) for restrictive or obstructive lungs; the disease syndrome may here either be specified by the user, or automatically identified by the respirator machine
  presettings for the therapy goal, for example minimization of breathing effort, stabilization of the CO2 value, optimization of patient comfort, avoidance of an intrinsic PEEP during the respiration, maintaining of a target value for tidal volume, alveolar tidal volume, minute volume, alveolar minute volume, treatment of obstructions of the upper airways, stabilization of the SpO2 value, ensuring a minimum or maximum pressure stroke, avoidance of dangerous situations, etc.; the presettings may be selected here by the user or stored permanently in the machine
  universal functions stored permanently in the machine for converting a breathing pattern into a suitable pressure profile, for example from a parallel plotting of pressure and flow rate on a time axis, from which corresponding pressure and flow rate values can be read off
  steps to optimize the synchronism of pressure profile and breathing effort of the patient, for example by extending or compressing the pressure profile steps to speed up or slow down the breathing
  optionally, the transform function may resort here to other signals from the outside, especially: SpO2, CO2, pulse wave, effort, heart rate, entry of respiration parameters by patient or medical staff, EMG of the respiratory muscles, breathing noises, breathing strain
  or to the results of the contour analyzer, for example in order to respond to obstructions of the upper airways by increasing/lowering the pressure profile, to control one of the mentioned volumes or to improve the synchronism of respiration and breathing effort of the patient by accelerating/slowing down the pressure profile or to lessen the intrinsic PEEP.

The pressure profile applicator (23) alternatively additionally optimizes the pressure profile for the current breath curve using the results of the curve analyzer:
  in particular to deal with deviations of the current breathing curve from the individual breathing pattern
  for example, the optimization may be done such that the deviation is supported or counteracted
  deviations are determined in particular in regard to magnitude of flow rate/volume, alveolar flow rate/volume or acceleration/slowing down of the breathing
  the optimization is done, for example, by a mathematical mapping, especially using the results of the contour analyzer or by scaling of the pressure profile ascertained by the mathematical mapping in terms of magnitude or duration/velocity.

FIG. 3a shows how a complete or partial breath, such as at least one inspiration and one expiration, is recorded by the sensor unit (15) for the determination of respiratory gas pressure and/or flow rate and/or volume, as a signal (25). The recording is done for example with >about 20 Hz, preferably >about 50 Hz or >about 90 Hz or 100 Hz and is saved in the memory (17). The signal used for the start of the recording may be, for example, the expiratory or inspiratory trigger (the effort of the patient to breathe out) recognized from the respiratory gas flow rate or pressure, or a few milliseconds after the expiratory trigger. Alternatively, a passing through zero after the expiratory trigger.

The signal (25) is plotted as the curve (28) taking into account the time (t). The curve (28) may then be used with lower resolution of, for example, less than 90 Hz, preferably less than 50 Hz, especially preferably less than 40 Hz or less than 30 Hz.

The curve analyzer (18) senses and/or analyzes the curve (28) of at least one signal (25) which stands in connection with the respiratory gas pressure, flow rate or volume, or which is the respiratory gas pressure, flow rate, or volume, and saves (17) this in memory. The curve (28) of the signal (25) may be downloaded from memory for this or the curve of the signal is processed "online" by the curve analyzer (18) during the determination by the sensor unit and only then saved in memory. The curve analyzer (18) is for example designed and set up to recognize a narrowing of the flow rate or volume signal in the inspiration as a flattening. The curve analyzer (18) is for example also designed and set up to recognize from the signal the volume, the I to E ratio, artifacts, mouth expiration, COPD breathing or Cheyne-Stokes breathing.

FIG. 3b shows: the cutout unit (19) selects defined time periods (30), or time periods (30) recognized from the curve (28), of the curve of at least one signal (25) from the memory (17). For example, the cutout unit (19) may select an inspiration, an expiration, a patient trigger, the volume, the I to E ratio, artifacts, mouth expiration, COPD breathing or Cheyne-Stokes breathing. The time periods (30) selected or identified by the cutout unit (19) are used by the breathing pattern analyzer (21) and/or the contour analyzer (20). This may be done at the same time or in succession.

The contour analyzer (20) is for example designed and set up to recognize from the curve (28) of the current time period the presence or absence of certain breathing states (26) or respiration states (27). For example, these are an inspiration (IN), an expiration (EX), a patient trigger, the volume, the I to E ratio, artifacts, mouth expiration, COPD breathing or Cheyne-Stokes breathing. For example, these are also the form of the inspiration and/or the expiration.

The breathing pattern analyzer (21) is for example designed and set up to ascertain the individual breathing pattern (24) of a patient from at least two curves (28). For example, the form of the inspiration and/or the expiration or the breath in the flow rate and/or volume and/or pressure curve of at least two curves (28) is/are compared here and joined to an individual standard contour for the patient, representing the individual breathing pattern (24) of a patient.

FIG. 3c shows: the transform function (22) converts the individual breathing pattern (24) or the curve (28) by at least one mathematical mapping (31) into a pressure profile (29) for the patient. The pressure profile (29) essentially takes into account, for example, the time (t) from the curve (28) and/or the time location of breathing states (26) or respiration states (27) in the breathing pattern (24)/the curve (28). The pressure profile (29) taking into account breathing pattern (24) or curve (28) specifies pressure levels (32, . . . 37) or pressure forms which are substantially synchronized in time to the breathing pattern (24) or the curve (28) and adapted to the patient's needs.

The pressure profile (29) defines, for example, an EPAP (32) which is increased to the IPAP (34) with an optional defined pressure ramp (33). The IPAP is decreased to the EPAP (32) with an optional defined pressure ramp (35). Optionally or additionally, the EPAP (32) is lifted to a slightly elevated expiratory level (36) with an optional defined pressure ramp. The slightly elevated expiratory level (36) affords the patient a slight counterpressure in the exhalation and serves for example to hold the alveoli open. The slightly elevated expiratory level (36) may be defined in dependence on the patient flow rate. After the level (36), at first the EPAP (32) may once again be specified by an optional defined pressure ramp (37). Alternatively, starting from the level (36), the IPAP (34) may be driven—optionally by a defined pressure ramp (33). In particular, the pressure profile may specify, for the levels (32) and/or (34) and/or (36), pressure waveforms instead of the pressure plateaus. In the profile (29) also no customary distinct pressure levels (32, . . . 37) may be discernible. The profile (29) runs according to the breathing pattern (24) or the curve (28) and is optimally adapted to the patient's needs.

The pressure profile applicator (23) actuates the pressurized gas source (14), in consideration of the pressure profile (29). The pressure profile applicator (23), using the results of the curve analyzer, can send the specified pressure profile, optimized to the curve of the breath and the nominal pressure, to the pressure source. The pressure profile applicator (23) actuates the pressurized gas source (14), in consideration of the pressure profile (29), for example so as to bring about an optimized synchronism with the patient's own breathing and/or to specify the most comfortable possible respiration and/or to have the slightest possible breathing effort of the patient and/or to prevent the formation of an intrinsic PEEP and/or to achieve a particular minute ventilation and/or to bring about an anticyclic servoventilation in treatment of certain pathological breathing patterns and/or to prevent obstructions of the airways and/or to achieve a certain tidal volume.

FIG. 4a and FIG. 4b show the steps according to the invention as in FIG. 3a and FIG. 3b. FIG. 4c shows, however: the transform function (22) converts the individual breathing pattern (24) or the curve (28) by at least one mathematical mapping (31) into a pressure profile (29) for the patient. The pressure profile (29) basically takes into account for example the time (t) from the curve (28) and/or the time position of breathing states (26) or respiration states (27) in the breathing pattern (24)/the curve (28). The pressure profile (29), taking into account breathing pattern (24) or curve (28) and optionally presettings, specifies a pressure form or a profile (29). No customary distinct pressure levels (32, . . . 37) are discernible. The profile (29) for example is synchronized in time to the breathing pattern (24) or the curve (28) and is optimally adapted to the patient's needs.

What is claimed is:

1. A device for respiration, wherein the device comprises at least one pressurized gas source for respiratory gas, a sensor unit for determining respiratory gas flow rate, a control unit, and a memory, the control unit comprising:

a curve analyzer, which is configured to determine and store in the memory a curve of at least one signal that is determined by the sensor unit, a transform function, which is configured to convert by at least one mathematical mapping the stored curve of the at least one signal determined by the sensor unit into a pressure profile and further is configured to use an individual breathing pattern of a patient, which is stored and formed as a function of at least two curves of the at least one signal, and a current breathing pattern of the patient, from the curve of the at least one signal, a pressure profile applicator, which is configured to actuate the pressurized gas source as a function of the pressure profile provided by the transform function;

and (i) wherein the device further comprises a cutout unit as well as a breathing pattern analyzer and/or a contour analyzer and the cutout unit is designed and set up to send defined time periods or time periods recognized from the curve of the at least one signal from the memory to the breathing pattern analyzer and/or to the contour analyzer and/or (ii) wherein the control unit further comprises a contour analyzer which is configured to recognize, as breathing states or respiration states, an inspiration and/or an expiration and/or a patient trigger and/or a volume and/or an I to E ratio and/or artifacts and/or mouth expiration and/or Cheyne-Stokes breathing.

2. The device of claim 1, wherein the control unit is configured to convert the curve of respiratory gas flow rate as a current breathing pattern of a patient into the pressure profile and to actuate the pressurized gas source as a function of the pressure profile.

3. The device of claim 1, wherein the transform function is additionally configured to use pre-settings of a user.

4. The device of claim 1, wherein the sensor unit is configured to record respiratory gas pressure and/or flow rate and/or volume with a resolution of at least 40 Hz.

5. The device of claim 1, wherein the control unit is configured to store the curve of the at least one signal in the memory with reduced resolution of less than 40 Hz.

6. The device of claim 1, wherein the device further comprises a cutout unit as well as a breathing pattern analyzer and/or a contour analyzer and the cutout unit is designed and set up to send defined time periods or time periods recognized from the curve of the at least one signal from the memory to the breathing pattern analyzer and/or to the contour analyzer.

7. The device of claim 1, wherein the control unit further comprises a contour analyzer which is configured to recognize, as breathing states or respiration states, an inspiration and/or an expiration and/or a patient trigger and/or a volume and/or an I to E ratio and/or artifacts and/or mouth expiration and/or Cheyne-Stokes breathing.

8. The device of claim 7, wherein the contour analyzer is configured to recognize certain breathing states or respiration states by pattern comparison.

9. The device of claim 1, wherein the control unit further comprises a breathing pattern analyzer, the breathing pattern analyzer or the transform function being configured to use a current curve of the at least one signal and an individual breathing pattern stored in the memory.

10. The device of claim 1, wherein the transform function is configured to convert, by the at least one mathematical mapping, an individual breathing pattern into the pressure profile, and in doing so also considers pre-settings of a user which are entered into the memory by an operating element or an operating and information system or an interface, and wherein the pressure profile considers the individual breathing pattern and pre-settings of a user.

11. The device of claim 10, wherein the pressure profile applicator is configured to actuate the pressurized gas source as a function of the pressure profile in such a way that an optimized synchronization with a patient's own breathing occurs.

12. The device of claim 10, wherein the pressure profile applicator is configured to actuate the pressurized gas source as a function of the pressure profile in such a way that a breathing effort of a patient is minimized.

13. The device of claim 10, wherein the pressure profile applicator is configured to actuate the pressurized gas source as a function of the pressure profile in such a way that a formation of an intrinsic PEEP is prevented.

14. The device of claim 10, wherein the pressure profile applicator is configured to actuate the pressurized gas source as a function of the pressure profile in such a way that an anticyclic servoventilation occurs.

15. The device of claim 10, wherein the pressure profile applicator is configured to actuate the pressurized gas source as a function of the pressure profile in such a way that a predetermined tidal volume is achieved.

16. The device of claim 1, wherein the pressure profile comprises a sequence of pressure levels and/or pressure waveforms and/or pressure plateaus and/or pressure ramps, substantially reflecting, at least in segments, corresponding segments of the respiration of a patient from the curve of the at least one signal and/or a breathing pattern.

17. The device of claim 16, wherein the corresponding segments include a frequency and/or an I/E ratio and/or a minute volume and/or inspirations and expirations.

18. A device for respiration, wherein the device comprises at least one pressurized gas source for respiratory gas, a sensor unit for determining respiratory gas flow rate, a control unit, and a memory, the control unit comprising:

a curve analyzer configured to sense, analyze and store in the memory a curve of at least one signal which stands in connection with or is the respiratory gas flow rate, a cutout unit configured to select one or more defined time periods recognized from the curve, of the curve of the at least one signal and to send them to a breathing pattern analyzer and/or a contour analyzer, a contour analyzer configured to recognize from the curve of the at least one signal of a current time period a presence or absence of certain breathing states or respiration states, a breathing pattern analyzer configured to ascertain an individual breathing pattern of a patient from at least two curves of the at least one signal, a transform function configured to convert by at least one mathematical mapping the curve of the at least one signal determined by the sensor unit into a pressure profile and further configured to use the individual breathing pattern of the patient, which is stored and formed as a function of at least two curves of the at least one signal, and a current breathing pattern of the patient, from the curve of the at least one signal, a pressure profile applicator configured to actuate the pressurized gas source as a function of the pressure profile provided by the transform function.

19. A device for respiration, wherein the device comprises at least one pressurized gas source for respiratory gas, a sensor unit for determining respiratory gas flow rate, a control unit, and a memory, the control unit comprising:

a curve analyzer configured to sense, analyze and store in the memory a curve of at least one signal which stands in connection with flow rate, a cutout unit configured to select one or more defined time periods recognized from the curve, of the curve of at least one signal stored in the memory and to send them to a breathing pattern analyzer and a contour analyzer, a contour analyzer configured to recognize from the curve of the at least one signal of a current time period that was sent to it by the cutout unit a presence or absence of certain acute breathing states or respiration states, a breathing pattern analyzer configured to ascertain an individual breathing pattern of a patient from at least two curves that were sent to it by the cutout unit, a transform function configured to convert by at least one mathematical mapping the curve of the at least one signal determined by the sensor unit into a pressure profile which is valid for a current or following breath and further configured to use the individual breathing pattern of a patient, which is stored and formed as a function of at least two curves of the at least one signal, and a current breathing pattern of the patient, from the curve of the at least one signal, a pressure profile applicator configured to use results provided by the curve analyzer to optimize a specified pressure profile to a curve of a breath and to send a nominal pressure to the pressure source.

20. The device of claim 19, wherein the transform function is configured to convert, by the at least one mathematical mapping, an individual breathing pattern into the pressure profile, and in doing so also considers pre-settings of a user which are entered into the memory by an operating element or an operating and information system or an interface, wherein the pressure profile considers the individual breathing pattern and pre-settings of a user, and wherein the pressure profile applicator is configured to actuate the pressurized gas source as a function of the pressure profile in such a way that an optimized synchronization with a patient's own breathing occurs and/or a breathing effort of a patient is minimized and/or a formation of an intrinsic PEEP is prevented and/or a predetermined minute ventilation is achieved and/or an anticyclic servoventilation occurs and/or a predetermined tidal volume is achieved.

* * * * *